United States Patent [19]

Mishra

[11] Patent Number: 5,703,487
[45] Date of Patent: Dec. 30, 1997

[54] DETECTION OF CHARGE DEFICIENT SPOT SUSCEPTIBILITY

[75] Inventor: Satchidanand Mishra, Webster, N.Y.

[73] Assignee: Xerox Corporation, Stamford, Conn.

[21] Appl. No.: 585,133

[22] Filed: Jan. 11, 1996

[51] Int. Cl.$^6$ .................................................. G03G 21/00
[52] U.S. Cl. ..................... 324/456; 324/501; 324/554; 324/72; 355/203
[58] Field of Search ............................... 324/456, 455, 324/501, 554, 452, 72; 355/203

[56] References Cited

U.S. PATENT DOCUMENTS

| | | | |
|---|---|---|---|
| 3,898,001 | 8/1975 | Hardenbrook | 355/203 |
| 4,134,137 | 1/1979 | Jacobs | 324/72 |
| 5,132,627 | 7/1992 | Popovic et al. | |
| 5,175,503 | 12/1992 | Mishra et al. | |
| 5,594,349 | 1/1997 | Kimura | 324/456 |

*Primary Examiner*—Ernest F. Karlsen
*Assistant Examiner*—Jose M. Solis

[57] ABSTRACT

A process is disclosed for ascertaining the microdefect levels of an electrophotographic imaging member comprising the steps of measuring either the differential increase in charge over and above the capacitive value or measuring reduction in voltage below the capacitive value of a known imaging member and of a virgin imaging member and comparing differential increase in charge over and above the capacitive value or the reduction in voltage below the capacitive value of the known imaging member and of the virgin imaging member.

9 Claims, 7 Drawing Sheets

DETECTION OF CHARGE DEFICIENT SPOT SUSCEPTIBILITY

BACKGROUND OF THE INVENTION

This invention relates in general to ascertaining projected microdefect levels of an electrophotographic imaging member and more specifically, to a process for comparing differential increase in charge or differential decrease of voltage from their capacitive values to determine charge deficiency spot susceptibility of electrophotographic imaging members.

In the art of electrophotography an electrophotographic plate comprising a photoconductive insulating layer on a conductive layer is imaged by first uniformly electrostatically charging the imaging surface of the photoconductive insulating layer. The plate is then exposed to a pattern of activating electromagnetic radiation such as light, which selectively dissipates the charge in the illuminated areas of the photoconductive insulating layer while leaving behind an electrostatic latent image in the non-illuminated area. This electrostatic latent image may then be developed to form a visible image by depositing finely divided electroscopic toner particles on the surface of the photoconductive insulating layer. The resulting visible toner image can be transferred to a suitable receiving member such as paper. This imaging process may be repeated many times with reusable photoconductive insulating layers.

The flexible photoreceptor belts are usually multilayered and comprise a substrate, a conductive layer, an optional hole blocking layer, an optional adhesive layer, a charge generating layer, and a charge transport layer and, in some embodiments, an anti-curl backing layer.

Although excellent toner images may be obtained with multilayered belt photoreceptors, it has been found that as more advanced, higher speed electrophotographic copiers, duplicators and printers were developed, there is a greater demand on copy quality. A delicate balance in charging image and bias potentials, and characteristics of toner/developer must be maintained. This places additional constraints on the quality of photoreceptor manufacturing, and thus, on the manufacturing yield. In certain combinations of materials for photoreceptors or in certain production batches of photoreceptor materials involved in the same kind of materials localized microdefect sites (size vary from about 50 to about 200 microns) can occur, using photoreceptors fabricated from these materials, where the dark decay is high compared to spatially uniform dark decay present in the sample. These sites appear as print defects (microdefects) in the final imaged copy. In charged area development, where the charged areas are printed as dark areas, the sites print out as white spots. These microdefects are called microwhite spots. In discharged area development systems, where the exposed area (discharged area) is printed as dark areas, these sites print out as dark spots in a white background. All of these microdefects which exhibit inordinately large dark decay are called charge deficient spots (CDS). Since the microdefect sites are fixed in photoreceptor, the spots are registered from one cycle of belt revolution to next. Charge deficiency spots have been a serious problem for a very long time in many organic photoreceptors. Little progress was made in developing photoreceptors which resist formation of charge deficient spots because of a lack of rapid techniques suitable for quickly assessing research laboratory samples. Charge deficiency spots are also a source of major yield losses in the production of photoreceptors. The only techniques known in the past for evaluation of the charge deficiency spots in a photoreceptor was through the formation of actual imaging machine prints or the use of a stylus scanner. Both of these techniques have serious flaws. Evaluation through machine testing cannot be accomplished on hand made samples because it is difficult to coat in a laboratory samples that are large enough to make a belt size sample usable to run in a machines. Also, contributions or "noise" from non-charge deficient spot related defects can overwhelm print quality during testing on imaging machines. Thus, any investigation of the charge deficient spots characteristics on imaging machines is very expensive because belts of a suitable size for testing on imaging machines must be fabricated on production equipment. The stylus scanner can be used for hand made devices but it is very slow (e.g. a 1 $cm^2$ area on a sample requires an hour or two to scan). Further, the stylus scanner test can be too sensitive and present serious problems in extrapolating the test results for large area performance (such as full page) from a realistically feasible measurement (e.g. 1 $cm^2$). Thus there is a need for a technique for testing for charge deficient spots which is quick and relatively insensitive to small variations in hand made devices and yet will produce reliable evaluations of charge deficient spot performance.

Whether these localized microdefect or charge deficient spot sites will show up as print defects in the final document will depend on the development system utilized and, thus, on the machine design selected. For example, some of the variables governing the final print quality include the surface potential of photoreceptor, the image potential of the photoreceptor, photoreceptor to development roller spacing, toner characteristics (such as size, charge and the like), the bias applied to the development rollers and the like. The image potential depends on the light level selected for exposure. The defect sites are discharged, however, by the dark discharge rather than by the light. The copy quality from generation to generation is maintained in a machine by continuously adjusting some of the parameters with cycling. Thus, defect levels could also change with cycling.

Cycling of belts made up of identical materials but differing in overall belt size and use in different copiers, duplicators and printers exhibited different microdefects. Moreover, belts from different production runs had different microdefects when initially cycled in any given copier, duplicator and printer. Since photoreceptor properties can vary from one production run to another even though they contain apparently identical materials it is important that a defective production run be detected as soon as possible to avoid excessive waste. Also, even sophisticated control system of any given imaging machine cannot compensate for an unacceptably severe microdefect population in a newly installed photoreceptor.

In the production of electrophotographic imaging members, particularly in web form, the complex nature of the manufacturing process renders unpredictable the susceptibility of microdefect levels of the coated web from batch to batch and from month to month. Thus, for example, microdefect levels can increase in a new production run due to changes in the manufacturing environment such as the installation or adjustment of new coating applicators or the initial use of a newly prepared batch of coating material for one of the many layers of the photoreceptors such as the hole blocking layer, charge generating layer, or charge transport layer. The susceptibility to microdefect levels is difficult to identify within a reasonable length of time subsequent to the point in time that the photoreceptor comes off the production line.

During production of multilayered belt photoreceptors, a test run is conducted on prepared photoreceptor test samples each time a major change is made to the production line. Examples of such major changes include the installation or adjustment of new coating applicators or the initial use of a newly prepared batch of coating material for one of the many layers of the photoreceptors such as the hole blocking layer, charge generating layer, or charge transport layer.

One technique for determining how many cycles photoreceptors from a specific production run will perform satisfactorily in a specific type of given copier, duplicator and printer without microdefects is to actually cycle the photoreceptor in the machine. Generally, it has been found that actual machine testing provides the most accurate prediction of the microdefect characteristics of a photoreceptor from a given batch. However, machine testing for photoreceptor life requires cutting a sheet from a double wide web, welding the sheet into a belt, installation in the machine, hand feeding of sheets by test personnel, and microscopic examination of the final copies. Thus, the machine testing approach can be extremely expensive and time consuming. Moreover, accuracy of the test results depends a great deal upon interpretations and behavior of the personnel that are feeding and evaluating the sheets. Further, since machine characteristics vary from machine to machine for any given model or type, reliability of the final test results for any given machine model must factor in any peculiar quirks of that specific machine versus the characteristics of other machines of the same model or type. Because of machine complexity and variations from machine to machine, the data from a microdefect test in a single machine is not sufficiently credible to justify the scrapping of an entire production batch of photoreceptor material. Thus, microdefect tests are normally conducted in three or more machines. Microdefect tests in copiers, duplicators or printers are time consuming, labor intensive and very expensive. Since a given photoreceptor may be used in different kinds of machines such as copiers, duplicator and printers under markedly different operating conditions, the microdefect prediction based on the machine print test of a representative test photoreceptor sample is specific to the actual machine in which photoreceptors from the tested batch will eventually be utilized will not necessarily predict what the print of that same type of photoreceptor would be in another different type of machine. Thus, for a machine print test, the test would have to be conducted on each different type of machine. This becomes extremely expensive and time consuming. Moreover, because of the length of time required for belt fabrication and machine testing, the inventory of stockpiled photoreceptors waiting approval based on print testing of machines can reach unacceptably high levels. For example, a batch may consist of many rolls with each roll yielding thousands of belts. Still further delays are experienced subsequent to satisfactory print testing because the webs must thereafter be formed into belts, packaged and shipped.

As described above, stylus scanner can be used for testing hand made photoreceptor devices but it is very slow (e.g. a 1 cm$^2$ area requires an hour or two to scan). Also, because it is an extremely sensitive technique, it poses a serious problem in extrapolating the results for large area performance (such as full page) from a realistically feasible measurement (e.g. 1 cm$^2$). Scanners have proved to be very slow for production line monitoring.

Another technique for determining whether a photoreceptor is capable of producing reliable copy quality to justify further processing is to fabricate the photoreceptors into belts and actually test how well they perform in customers' machines. Feedback in the form of reports from customers or performance evaluation reports from repair persons in the field are not always reliable because the tests are not conducted under controlled conditions and the cause of failure may be due to factors other than electrical such as the dark decay properties of the photoreceptor. Reliance on field tests can result in extensive delays, and, if the performance is unsatisfactory, will understandably aggravate customers. Moreover, reports from repair persons can be difficult to interpret because belt life may be affected by the peculiarities of the given machine involved, other factors affecting belt life that are unrelated to the electrical factors tested by the process of this invention, and the like. Also, data input from repair persons in the field requires one to accumulate and interpret the input over a period of time. This long delay can result in the introduction of large numbers of defective photoreceptor belts into the field.

To avoid fabricating an entire roll of photoreceptor material prior to testing, one can fabricate only a small part of the roll and test the resulting photoreceptor. If the test sample performs well during the test, the entire roll can thereafter be coated. However, testing by means of prior art techniques can still result in long delays because such testing required large amounts of time. Evaluation through machine testing cannot be accomplished on hand made samples because it is difficult to coat in a laboratory samples that are large enough to make a belt size sample usable to run in a machines. Thus, a production line could stand idle until the favorable test results were received. Since the expected point quality of a photoreceptor is extremely important from the viewpoint of manufacturing rate, inventory size, customer satisfaction and numerous other reasons, there is a great need for a system for rapidly determining the service life of flexible belt photoreceptors before initiating a full stage production run of flexible belt photoreceptors.

Thus there is a need to identify photoreceptors which resist formation of charge deficient spots (microdefects).

INFORMATION DISCLOSURE STATEMENT

U.S. Pat. No. 5,175,503 to Mishra et al, issued Dec. 29, 1992—A process is disclosed for ascertaining the projected imaging cycle life of an electrophotographic imaging member including the steps of (a) providing at least one electrophotographic imaging member having a cycling life of a known number of imaging cycles, the imaging member comprising an electrically conductive layer and at least one photoconductive layer, (b) repeatedly subjecting the electrophotographic imaging member to cycles comprising electrostatic charging and light discharging steps, (c) measuring dark decay of the photoconductive layer during cycling until the amount of dark decay reaches a crest value, (d) establishing with the crest value a reference datum for dark decay crest value versus imaging cycles, (e) repeatedly subjecting a virgin electrophotographic imaging member to aforesaid cycles comprising electrostatic charging and light discharging steps until the amount of dark decay reaches a crest value which remains substantially constant during further cycling, and (f) comparing the dark decay crest value of the virgin electrophotographic imaging member with the reference datum to ascertain the projected cycling life of the virgin electrophotographic imaging member.

U.S. Pat. No. 5,132,627 to Popovic et al, issued Jul. 21, 1992—A process is disclosed for ascertaining electrical discharge properties of an electrophotographic imaging member including the steps of (a) providing at least one electrophotographic imaging member comprising an electrically conductive layer and at least one photoconductive layer, (b) contacting the surface of the electrophotographic imaging member with a substantially transparent electrode and applying an electric potential or an electric current to form an electric field across the photoconductive layer, (c) terminating the applying of the electric potential or the electric current, (d) exposing the photoconductive layer to activating radiation to discharge the electrophotographic imaging member, (e) repeating steps (b), (c) and (d), and (f) measuring the potential across the photoconductive layer during steps (b), (c) and (d) as a function of time by means of an electrostatic meter coupled to the electrode. Also, disclosed is apparatus for ascertaining electrical discharge properties of an electrophotographic imaging member including (a) means to support an electrophotographic imaging member comprising an electrically conductive layer and at least one photoconductive layer, (b) means for applying an electric potential or electric current to a substantially transparent electrode on the electrophotographic imaging member to form an electric field across the photoconductive layer, (c) means for terminating the applying of the electric potential or the electric current, (d) an electrostatic voltmeter probe coupled to the means for applying an electric current to the electrode, (e) means for exposing the photoconductive layer through the substantially transparent electrode to activating radiation to discharge the electrophotographic imaging member to a predetermined level, and (f) means for exposing the photoconductive layer to activating radiation to fully discharge the electrophotographic imaging member.

Thus, there is a continuing need for a system for ascertaining charge deficiency spot susceptibility of electrophotographic imaging members.

SUMMARY OF THE INVENTION

It is, therefore, an object of the present invention to provide an improved process for assessing the microdefects of an electrophotographic imaging member which overcomes the above-noted deficiencies.

It is another an object of the present invention to provide an improved process for ascertaining charge deficiency spot susceptibility of electrophotographic imaging members.

It is yet another object of the present invention to provide an improved process for comparing differential increases in charge value from their capacitive value of a virgin electrophotographic imaging member against a standard while maintaining the same charge fixed for both imaging members.

It is yet another object of the present invention to provide an improved process for comparing differential increase in charge value from the capacitive value of a virgin electrographic imaging member against a standard while maintaining the voltage fixed for both imaging members.

It is yet another object of the present invention to provide an improved process for comparing differential reduction of voltage value from their capacitive value of a virgin electrographic imaging member against a standard while maintaining the same charge fixed for imaging members.

It is yet another object of the present invention to provide an improved process for comparing differential reduction of voltage from their capacitive value of a virgin electrographic imaging member against a standard while maintaining the same voltage fixed for both imaging members.

It is yet another object of the present invention to provide an improved process for comparing differential reduction of voltage from their capacitive value of a virgin electrographic imaging member against a standard while keeping the voltage on both devices same.

It is still another object of the present invention to provide an improved process for more accurately assessing the microdefects of an electrophotographic imaging member.

It is another object of the present invention to provide an improved process for more accurately assessing the projected microdefects population of an electrophotographic imaging member independent of machine interactions.

It is yet another object of the present invention to provide an improved process for determining the dark decay related failure mode of an electrophotographic imaging member.

It is yet another object of the present invention to provide an improved process for determining the dark decay related failure mode of an electrophotographic imaging member in a safer manner.

The foregoing objects and others are accomplished in accordance with this invention by providing a process for ascertaining the microdefect levels of an electrophotographic imaging member comprising the steps of measuring either the differential increase in charge over and above the capacitive value or measuring reduction in voltage below the capacitive value of a known imaging member and of a virgin imaging member and comparing differential increase in charge over and above the capacitive value or the reduction in voltage below the capacitive value of the known imaging member and of the virgin imaging member.

More specifically, the process of this invention can include the following steps:

(a) providing at least a first electrophotographic imaging member having a known differential increase in charge value from the capacitive value, the imaging member comprising an electrically conductive layer and at least one photoconductive layer, (b) repeatedly subjecting the at least one electrophotographic imaging member to cycles comprising electrostatic charging and light discharging steps while keeping the applied voltage fixed across the imaging member, (c) measuring dark decay of the at least one photoconductive layer during cycling until the amount of dark decay reaches a crest value, (d) measuring the change needed to charge the imaging member to the set voltage when the dark decay has reached a crest value, (e) repeating step (b) with successively increasing applied voltage, (f) repeating step (c) at each selected step of applied voltage, (g) repeating step (d) after step (c) for each selected value of applied voltage in step (e), (h) plotting a graph of volts (y-axis) vs charge (x-axis) for the sample, (i) determining the capacitive charging V-Q relationship for the lower voltage settings, (j) determining incremental charge needed over and above the capacitive value to charge the photoreceptor to a set higher voltage which gives a high field (usually this field is chosen between about 60 v/micrometer to about 80 volts/micrometer).

(k) alternatively, instead of step [;] one may determine differential reduction in voltage (DVR) below the capacitive value (usually the voltage at which this is calculated is chosen at a higher field between about 60 volts/micrometer to 80 volts/micrometer.

(l) in another version of this, steps (j) and (k) can be performed at a definite setting of charge usually chosen to give a higher field between about 60 volts/micrometer to 80 volts/micrometer.

(m) repeatedly subjecting a virgin electrophotographic imaging member to the aforementioned steps from (a) through (l).

(n) establishing for the virgin electrophotographic imaging member a datum for differential increase in charge over and above the capacitive value, the value of voltage at which the calculation is made being the same as in step (j) or the charge being the same as selected in step (l) for the standard sample free of defects.

(o) establishing for the virgin electrophotographic imaging member a datum for differential voltage reduction (DVR) below the capacitive value, the value of voltage at which this calculation is made being the same as in steps (k) or (l), the charge being the same as selected in step (l) for the standard sample free of defects.

(p) comparing the differential increase in charge (DIC) value or the differential voltage reduction (DVR) of the virgin electrophotographic imaging member with the known DIC or DVR value to ascertain the projected microdefect levels of the virgin electrophotographic imaging member.

BRIEF DESCRIPTION OF THE DRAWINGS

A more complete understanding of the present invention can be obtained by reference to the accompanying drawings wherein.

These figures merely schematically illustrate the invention and are not intended to indicate relative size and dimensions of the device or components thereof.

DETAILED DESCRIPTION OF THE DRAWINGS

The test apparatus utilized to carry out the process of this invention is described in detail in U.S. Pat. No. 5,175,503 and U.S. Pat. No. 5,132,627, the entire disclosures of these patents being incorporated herein by reference.

Figure 1:
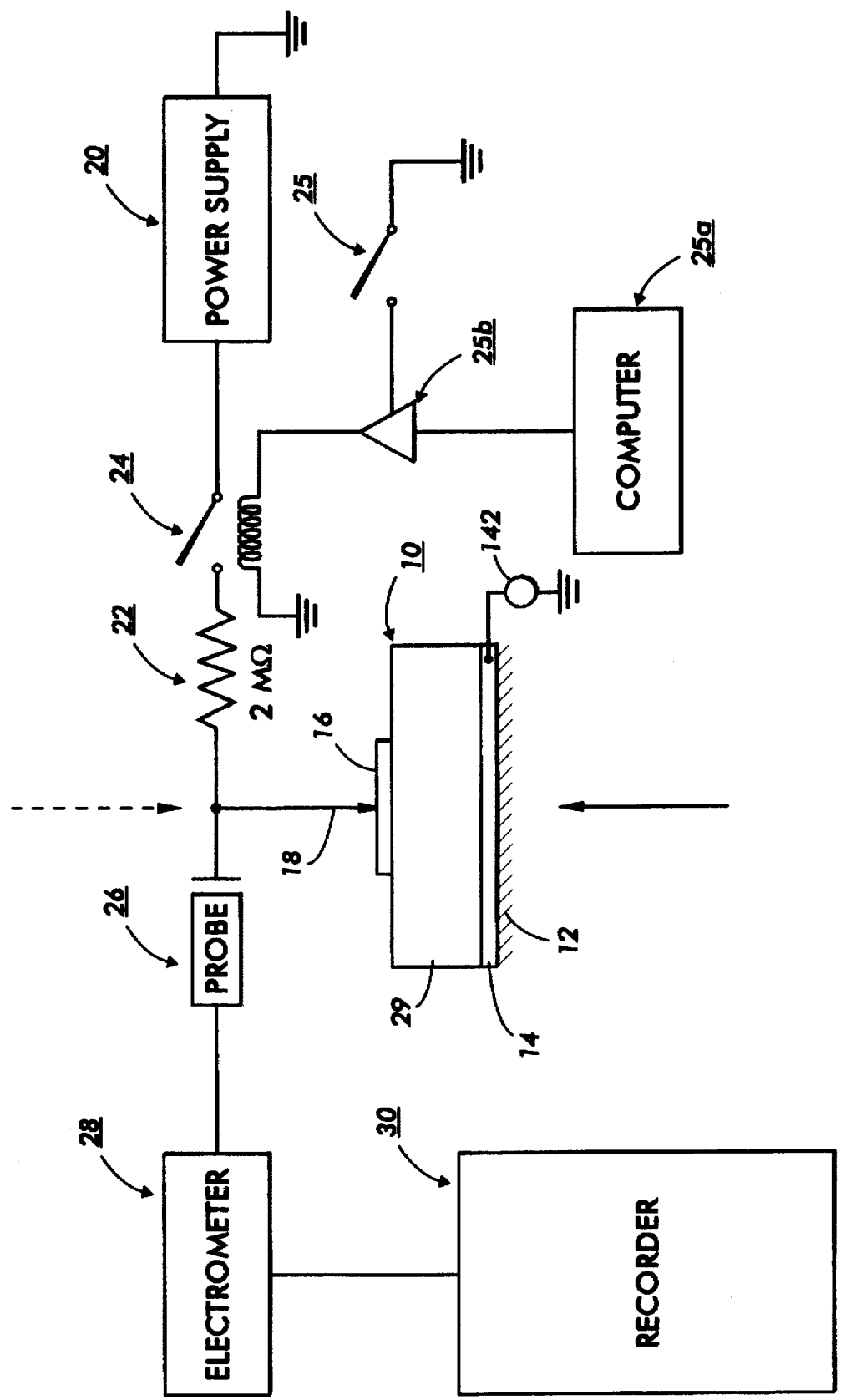
FIG. 1 is a schematic illustration of an electrical circuit employed in the system of this invention.

Referring to FIG. 1, a schematic, including an electrical circuit, employed in the system of this invention is shown in which a photoreceptor 10 rests on a substantially transparent support member 12. The electrically conductive surface of substrate layer 14 of photoreceptor 10 is electrically substantially transparent vacuum deposited metal electrode 16 on its upper surface. An electrical connector 18 connects electrode 16 with a high voltage power supply 20 through resistor 22 when a controller such as a relay 24 is closed. Relay 24 is activated by a signal from computer 25a which is fed through a FET 25b. The gate of the FET 25b is closed by the magnetically activated reed switch 25. The magnetic switch is closed when the lid of the apparatus is closed. A probe 26 (e.g. Model 17211, available from Trek) from a conventional electrometer 28 (e.g. Model 3666, available from Trek) senses, via electrical connector 18, the electrical field imposed across photoconductively active layer 29 during testing of photoreceptors. Photoconductively active layer 29 may comprise a single layer such as photoconductive particles dispersed in a binder or multiple layers such as a photoconductive charge generating layer and a charge transport layer. The output of electrometer 28 is fed to chart recorder 30 (e.g. Model TA2000, available from Gould) or to a suitable computer (not shown, e.g. IBM compatible computer). Exposure light (represented by dashed arrow) is periodically transmitted through substantially transparent electrode 16 to photoreceptor 10 and, similarly, erase light (represented by solid arrow) is periodically transmitted to photoreceptor 10 through transparent support member 12. The charge Q is measured by the coulomb meter 14a.

Figure 2:
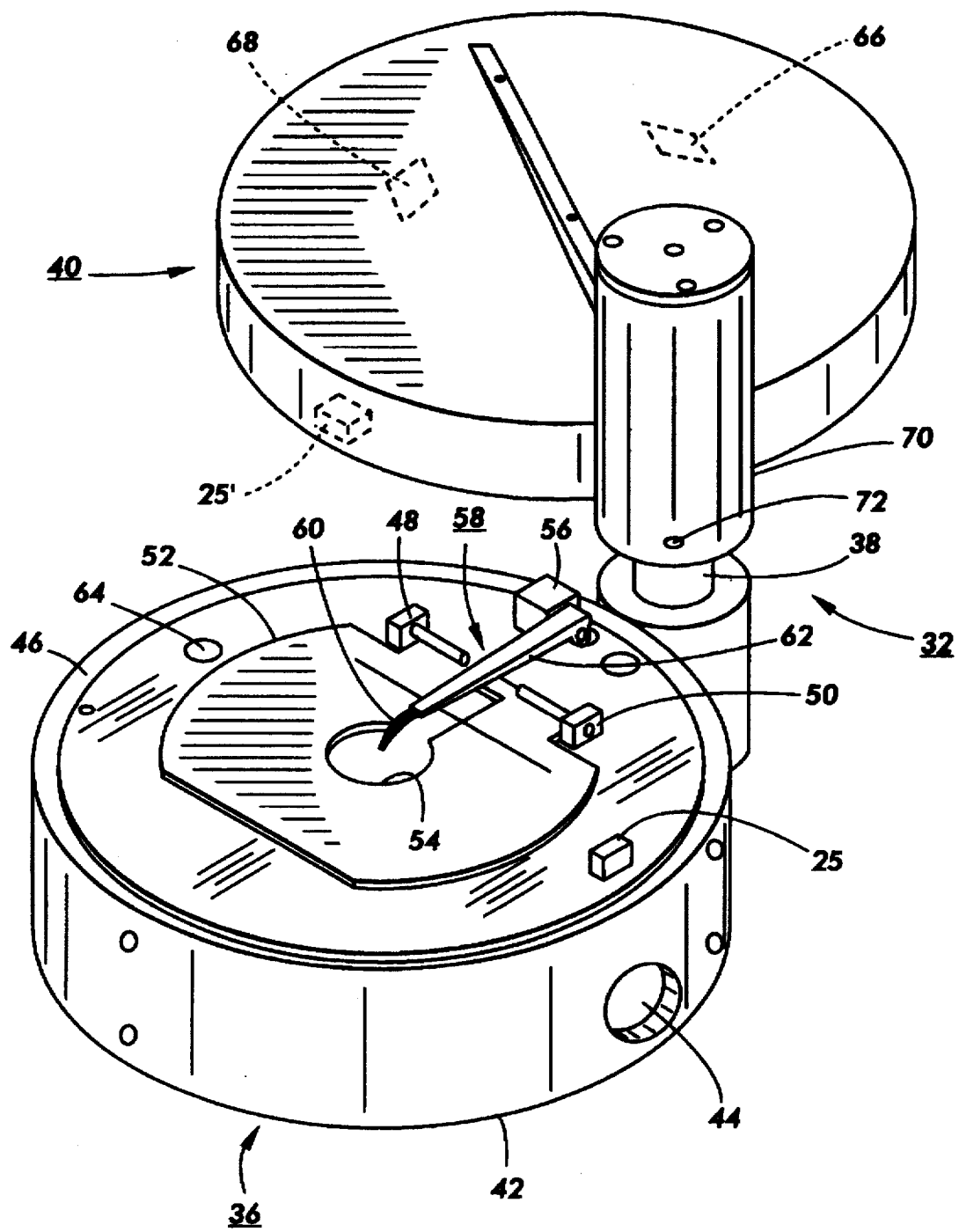
FIG. 2 is an isometric illustration of an apparatus employed in the system of this invention.

In FIG. 20 a motionless scanner apparatus 32 is illustrated comprising a base assembly 36 which supports a vertical post 38 which in turn supports a cylindrical lid assembly 40. Base assembly 36 comprises a light tight cylindrical housing 42 having a opening 44 on one side to allow entry of power cords leading to an erase light source (not shown) located within housing 42 or to admit erase light from a suitable external source (not shown) and another opening on the other side (not shown) to allow entry of power cords leading to a light source (not shown) located within housing 42 or to admit exposure light from a suitable external source (not shown). Any suitable erase light source may be utilized. Typical erase light sources include broadband flash tubes such as xenon lamps. Although optional, it is preferred to tune the light source to the spectral response of the photoreceptor by suitably filters. As indicated above, the light from either the erase light exposure source or the exposure light source may be supplied by a source located within base assembly 36 or fed into base assembly 36 from an external source by any suitable means. Typical light feeding means include, for example, light pipes and the like. Secured to the flat glass upper platen 46 of cylindrical housing 42 are a pair of hinge post 48 which receive hinge pins 50 of pivotable flat ground plate 52. Flat glass upper platen 46 is transparent and electrically insulating. When a sample of photoreceptor 10 (see FIG. 1) is mounted for testing under ground plate 52, aperture 54 encircles but does not touch the circular vacuum deposited metal electrode 16 (see FIG. 1). Ground plate 52 is electrically grounded and contacts the upper surface of the photoreceptor sample to flatten the sample and to electrically ground the electrically conductive surface of substrate layer 14 of photoreceptor 10. Grounding of the conductive surface of layer 14 of photoreceptor 10 occurs because, mounting under ground plate 52, a strip of the photoconductively active layer 29 along one edge of photoreceptor 10 is scraped away to expose a portion of the electrically conductive surface of substrate layer 14. A thick conductive silver coating (not shown) is applied to the exposed strip of conductive surface. Since the upper surface of the deposited silver coating extends beyond the upper surface of photoconductively active layer 29, ground plate 52 contacts the silver coating when it rests on the upper surface of photoreceptor 10 thereby grounding the electrically conductive surface of substrate layer 14. Secured to the flat upper surface 46 of cylindrical housing 42 is hinge post 56 which supports pivotable electrical connector arm 58. Pivotable electrical connector arm 58 has an electrically conductive finger 60 which can be swung into and out of contact with the circular vacuum deposited metal electrode 16 (see FIG. 1) when a sample of photoreceptor 10 (see FIG. 1) is mounted for testing under ground plate 52. Ground plate 52 is connected to ground. When the free end of ground plate 52 is lifted to mount the sample, ground plate 52, connected to hinge pins 50, contacts and lifts the high voltage arm 62 and thus electrically grounds it. Thus, if other safety switches fail, the power supply will be short circuited and the relay in the power supply will switch it off. Lid assembly 40 swivels around and slides vertically on vertical post 38 and is adopted to fit as a light tight lid on top of base assembly 36. A hole 64 is positioned in flat glass upper platen 46 adjacent to the exposure light opening (not shown) on the side of base assembly 36 diametrically opposite from opening 44. Mounted on the roof of the hollow interior of lid assembly 40 are two exposure light mirrors 66 and 68. When cylindrical lid assembly 40 is aligned with and resting on base assembly 36, exposure light mirror 66 is positioned to horizontally reflect exposure light (projected upwardly from hole 64) to mirror 68 which in turn reflects the exposure light downwardly through the circular vacuum deposited metal electrode 16 (see FIG. 1) on photoreceptor samples. A magnetically activated reed switch 25 comprising mounted on the edge of flat glass upper platen 46 and permanent magnet 25' attached to the inside surface of lid assembly 40. Permanent magnet 25' is positioned to ensure that when lid assembly 40 is closed, magnet 25' rests over and activates reed switch 25 to close it. Closure of reed switch 25 causes, with the aid of suitable means such as a VFet transistor 25b shown in FIG. 1, high voltage relay 24 (see FIG. 1) to be ready to receive a trigger pulse from the computer 25a. When lid assembly 40 is opened, magnet 25' is moved away from reed switch 25, thereby opening reed switch 25 and turning off the VFet transistor 25b and high voltage relay 24, thus preventing accidental shock when an operator removes or inserts samples. Cylindrical lid assembly 40 is supported on vertical post 38 by a journal box 70. A guide pin 72 is press fitted into a hole in the side journal box 70. The pin projects beyond the inner surface of journal box 70 into a slot (not shown) machined into the periphery of vertical post 38. The slot is similar in shape to an inverted "L" so that when cylindrical lid assembly 40 is aligned directly over base assembly 36, pin 72 rides in the vertical portion of the inverted "L" shaped slot so that lid assembly 40 may be moved vertically toward and away from base assembly 36. When cylindrical lid assembly 40 is lifted upwardly from a "closed" or "test" position until pin 72 has shifted to the upper limit of the slot, lid assembly 40 can be swung horizontally with pin 72 riding in the horizontal portion of the inverted "L" shaped slot until lid assembly 40 reaches an "open", "load" or "unload" position relative to base assembly 36 similar to the position illustrated in FIG. 2.

In operation, with cylindrical lid assembly 40 in the "open" position, the free end of pivotable electrical connector arm 58 is pushed away from flat glass upper platen 46 by the plate 52 when it is lifted to mount the sample. In this position, the electric conducting finger 60 is grounded through plate 52. Because of the high voltages involved, the electrically conductive finger 60 and pivotable flat ground plate 52 should be electrically grounded during insertion and removal of a photoreceptor sample in the testing apparatus. Thus, when the pivotable flat ground plate 52 for flattening photoreceptor samples is raised to either insert or remove a photoreceptor sample, such raising automatically grounds the high voltage probe 60. This is a back-up safety feature because the arm 60 is also disconnected by safety switch 25 as the lid is lifted up. A sample of flexible photoreceptor is placed on flat glass upper platen 46. The sample is slightly smaller than the pivotable flat ground plate 52. The sample has previously been prepared (see above and hereinafter) for testing and carries a raised strip of thick conductive silver coating (not shown) along one edge of photoreceptor 10 to establish electrical contact with the conductive surface of substrate layer 14. Since the upper surface of the thick silver coating extends beyond the upper surface of photoconductively active layer 29, it contacts the lower surface of ground plate 52 to electrically ground the electrically conductive surface of substrate layer 14 of photoreceptor 10 when plate 52 is lowered to flatten photoreceptor 10. Photoreceptor 10 also carries a thin, substantially transparent (i.e. semitransparent) circular vacuum deposited metal electrode 16 of a suitable metal such as gold (see FIG. 1) on its upper surface that is encircled by, but not in physical contact with, aperture 54. The free end of pivotable electrical connector arm 58 is pivoted downwardly toward and into contact with metal electrode 16. Cylindrical lid assembly 40 is pivoted and lowered to produce a light tight fit between lid assembly 40 and base assembly 36. The assembly 40 closes the switch 25 and activates VFet transistor 25b. The computer pulse then can close the relay 24 for a desired, preselected time interval. A voltage pulse is applied by the activation of relay 24 for the preselected time interval, typically 100 milliseconds, and the dark decay of photoreceptor 10 is measured with probe 26 (see FIG. 1) and electrometer 28 (see FIG. 1) during the dark cycle following the voltage pulse but prior to light being emitted by the erase light. The voltage pulse may be at a fixed level, typically between levels to give a field of between about 45 volts/micrometer and about 80 volts/micrometer from one cycle to another or may be gradually increased to vary the field, typically from 10 volts/micrometer to 80 volts/micrometer, during the assessment period. A satisfactory voltage pulse range for both the fixed level or gradual increase embodiments is between about 5 volts/micrometer and about 100 volts/micrometer, but below dielectric breakdown. The charge Q is measured by a coulomb meter 14a Measurement taken at a fixed time period after termination of the voltage pulse, typically 1–2 seconds, and the measurement is recorded on chart recorder 30. The voltage V and charge Q are also recorded on the multichannel chart recorder 30. If desired, any suitable computer (not shown) may be utilized instead of a chart recorder to monitor voltage during cycling. Photoreceptor 10 is then optionally exposed to the exposure light projected upwardly from hole 64 to mirror 66, then to mirror 68, and finally downwardly through the circular vacuum deposited metal electrode 16 (see FIG. 1) on the photoreceptor sample. To maximize light exposure through the electrode 16, the size of pivotable electrical connector arm 58 and electrically conductive finger 60 should be relatively small so that light exposure through electrode 16 is maximized. The entire sample is thereafter flood exposed by an erase light source (not shown) located within housing 42 or transmitted through opening 44 from a suitable source (not shown), through flat glass upper platen 46, through transparent support member 12, and through the electrically conductive surface of substrate layer 14. It is important that during the cycling, the erase light has sufficient intensity stability so that variable readings and other errors are avoided during measurements of photoreceptors from one batch to another. Since the erase light intensity should remain constant in order to give predictable readings, a suitable sensor (not shown) such as a photodiode may be utilized to detect changes in the light intensity so that the light may be either replaced or adjusted to ensure constant light intensity during the exposure and erase cycles. If desired, suitable filters (not shown) may be interposed between the erase light and photoreceptor to more accurately simulate the light frequency used in the copier, duplicator or printer in which the photoreceptor will ultimately be employed. Also, a conventional corotron or scorotron may be substituted for the electroded arrangement described above to apply an electrical charge to the photoreceptor sample. This is conveniently accomplished on a drum or flat plate scanner.

It was found with early experimental versions of the apparatus that reproducible results by different personnel conducting the tests on a variety of samples could not be achieved. The apparatus of this invention ensures that the photoreceptor is flat; ensures that the contact electrode is placed in the center of the metal electrode with minimum shadow effect; and ensures that the light utilized for erasure is at a constant intensity from sample to sample. These features enhance the accuracy of tests involving different test samples.

In the process of this invention, the typical photoreceptor tested comprises a flexible supporting substrate layer, an electrically conductive layer, an optional blocking layer, an optional adhesive layer, a charge transport layer and a charge generating layer. Rather than requiring large amounts of test material, the test sample may be quite small in size, e.g., 2 inches by 4 inches. It has been found that a test of one small sample is an effective test for an entire roll or batch of rolls prepared from the same coating batch. The photoreceptor is solvent treated along one edge to dissolve and remove parts of the charge transfer layer, charge generating layer and adhesive layer to expose part of the electrically conductive layer. A electrically conductive layer of silver paint is applied to the exposed surface of the electrically conductive layer for purpose of forming a terminal contact point for application of an electrical bias to the conductive layer.

A predetermined area of the imaging surface of the photoreceptor not treated with solvent is coated with a thin vacuum deposited gold or other suitable metal layer through a mask or stencil having an appropriate size and shaped opening to form another electrode so that an electrical bias can be applied across the photoconductive layers of the photoreceptor from the gold electrode to the electrically conductive layer. The thickness of the metal electrode from one photoreceptor sample to another should be the same to ensure that the amount of light transmission is also the same as that used for the obtaining of the comparison data to establish a standard. The metal electrode may be of any suitable size and shape, but the size and shape should be the same from one photoreceptor sample to another to ensure accurate comparisons.

As described above, the process of this invention is especially useful for assessing virgin samples of photoreceptors from the output of a manufacturing line to determine the severity level of microdefects of the virgin photoreceptor. The expression "Differential Increase of Charge" refers to the increase in charge needed to charge a photoreceptor to a predetermined voltage over and above the capacitive charge needed for that voltage. The extra charge is needed due to dark excessive charge from the generation layer and lower layers. At sufficiently higher voltages the discrete spots which are potential charge deficient spots are the main source of this dark excessive charge. The expression "Differential Reduction of Voltage" refers to the decrease in voltage from the capacitive voltage due to the dark excessive charge discussed above.

Figure 3:
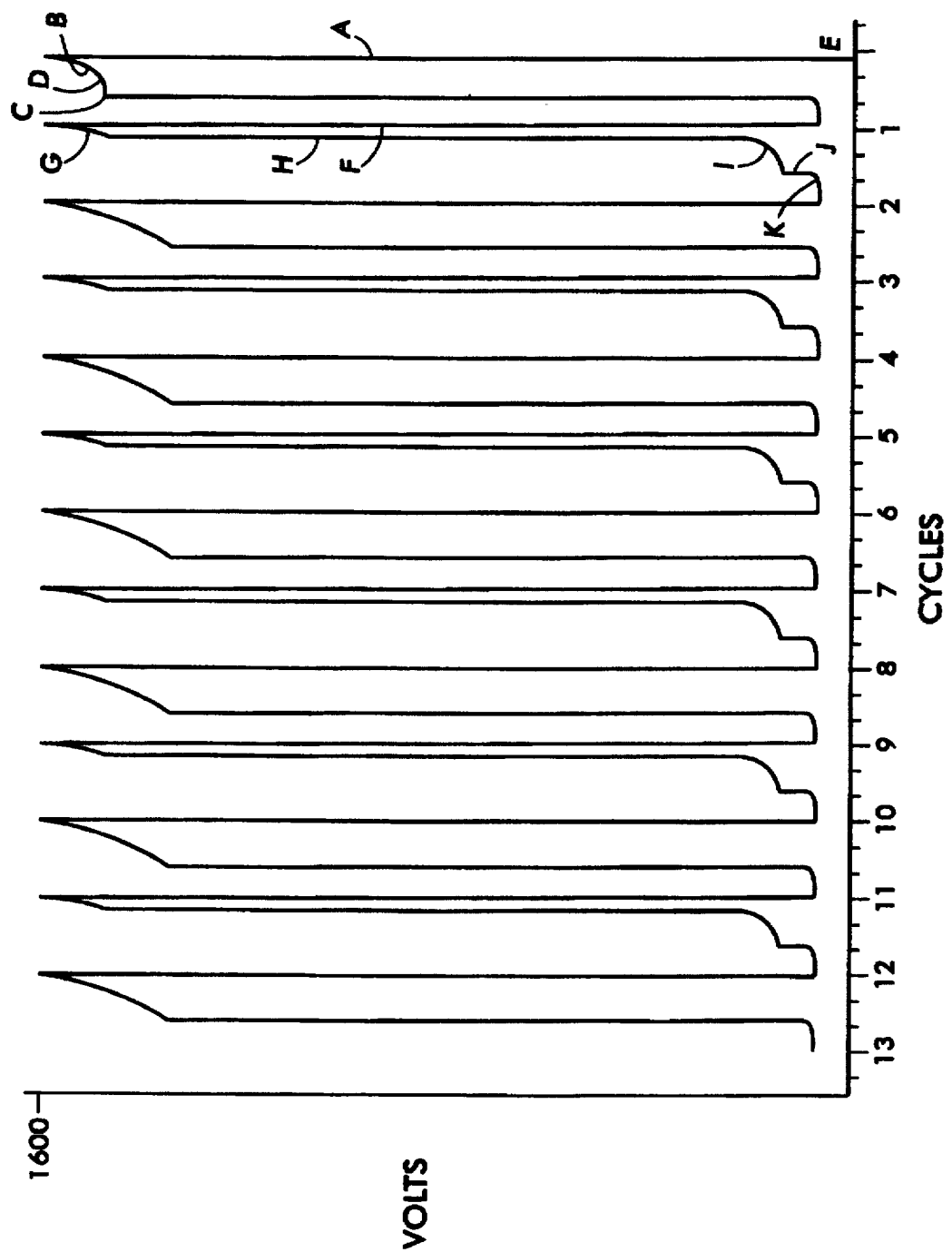
FIG. 3 is a chart illustrating cycles involving charging, dark decay and discharging effects.

In the embodiment of this invention where the charging voltage across the sample is kept constant, the dark decay generally increases with cycling at a fixed voltage but levels off at a crest value after a few cycles. Typically, it takes about 5 to about 20 cycles for stable dark decay to be achieved, i.e. attainment of a crest value, but may vary somewhat depending on the specific sample tested. The dark decay is continuously monitored on a recorder or suitable computer. This stable dark decay or crest value is measured as illustrated in FIG. 3 wherein charging to 1600 volts is shown by the vertical line (A) on the right hand side of the figure. Dark decay begins as soon as the initial charging is completed and is represented by curve (B), The potential of the charged areas of the electrostatic latent image that would be formed during the image exposure step of a normal imaging cycle is close, but prior to the beginning of the erase exposure step at point (C). Thus, the potential of the charged areas of the electrostatic latent image would be located at about point (D) on the dark decay curve (B). Although dark decay to point (D), or any other point measured at some fixed time after termination of charging, may be utilized for determining the crest values for electrophotographic imaging members, it is usually more convenient and more accurate to measure dark decay to point (C) where the erase exposure step begins. Upon termination of the erase step, the residual charge on the photoreceptor dark decays further as illustrated by curve (E). Vertical line (F) represents the charging step for the second cycle. Thus, the first cycle is represented by curves and points (A) through (E) to (F). Dark decay from termination of charging to the point of image (background) exposure is represented by curve (G). Discharge during the image (background) exposure is represented by curve (H). Upon termination of the image (background) exposure step, the residual charge on the photoreceptor dark decays further as illustrated by curve (I) until the erase exposure step shown by (J). Upon termination of the erase step, the residual charge on the photoreceptor dark decays further as illustrated by curve (K). Thus, the second cycle is represented by curves and points (F) through (K) to the next charging step. This image (background) exposure cycle can be omitted from the test cycling procedure but the crest value of dark decay would be higher. Although the image (background) exposure cycle is used above during every other cycle, one can use the exposure cycle for every cycle and omit the image (background) cycles.

The amount of dark decay between termination of charging and image (background) or erase exposure reaches a crest value during repeated cycling. The measurement of charge is made only after crest value of dark decay is reached. Satisfactory projections of microdefects (i.e. charge deficient spots) may be obtained when this crest value is reached when the change in dark decay from cycle to cycle at corresponding points (whether from charge-erase cycle to charge-erase cycle or from charge-image The amount of dark decay between termination of charging and image (background) or erase exposure reaches a crest value during repeated cycling. Satisfactory projections of microdefects (i.e. charge deficient spots) may be obtained when this crest value is selected when the change in dark decay from cycle to cycle at corresponding points (whether from charge-erase cycle to charge-erase cycle or from charge-image (background) exposure-erase cycle to charge-image (background) exposure-erase cycle) is less than about 10 volts. Preferably, the crest value is selected when the change in dark decay from cycle to cycle is less than about 5 volts. Optimum accuracy is achieved when the crest value is selected when the change in dark decay from cycle to cycle is less than about 5 volts. These cycling readings are obtained for electrophotographic imaging members having an acceptable microdefects population. Readings from at least two photoreceptors having a known number of microdefects, one having a better microdefects population than the other, may be used to obtain a known differential increase in charge values or differential reduction in voltage values for the two. These define a first reference datum and a second reference datum for the photoreceptor having a known number of microdefects for purposes of comparison with photoreceptors having an unknown microdefects population. This technique is used to ascertain the projected microdefect levels of an electrophotographic imaging member when neither photoreceptors have microdefects that would meet a threshold acceptance criterion for microdefects. Alternatively, acceptable and unacceptable photoreceptors may be identified by comparison to a known standard that has an acceptable threshold microdefects population.

Thus, the process of this invention for ascertaining the projected microdefect levels of an electrophotographic imaging member generally comprises the steps of (a) providing at least a first electrophotographic imaging member having a known differential increase in charge value over and above the capacitive value or difference in reduction in voltage below the capacitive value, the imaging member comprising an electrically conductive layer and at least one photoconductive layer, (b) repeatedly subjecting the at least one electrophotographic imaging member to cycles comprising electrostatic charging and light discharging steps, (c) measuring dark decay of the at least one photoconductive layer during cycling until the amount of dark decay reaches a crest value, (d) measurement of charge and voltage after crest value has been reached, (e) repeating step (d) at successive increasing values of voltage and charge to establish a Q-V relationship to cover range of fields from 5 volts/micrometer and about 80 volts/micrometer, fitting a straight line to Q-V data in the small field range. Usually this is below 20 to 25 volts/micron. This represents a capacitive charging Q-V relationship, (f) determining the differential increase in charge over the capacitive charge or reduction of voltage below the capacitive value at a setting of voltage or charge which gives field between 60 volts/micrometer and about 80 volts/micrometer, (g) repeatedly subjecting a virgin electrophotographic imaging member to aforesaid cycles comprising electrostatic charging and light discharging steps until the amount of dark decay reaches a crest value for the virgin which remains substantially constant during further cycling, (h) repeat of step (e) for the virgin photoreceptor, (i) establishing with the crest value for the virgin electrophotographic imaging member a reference datum for differential increase of charge over the capacitive value or reduction in voltage below the capacitive value at same setting of voltage and charge as in step (f), (j) comparing the differential increase in charge or differential reduction in voltage value of the virgin electrophotographic imaging member with the known differential increase in charge or differential reduction of voltage value to ascertain the projected microdefect levels of the virgin electrophotographic imaging member.

Figure 4:
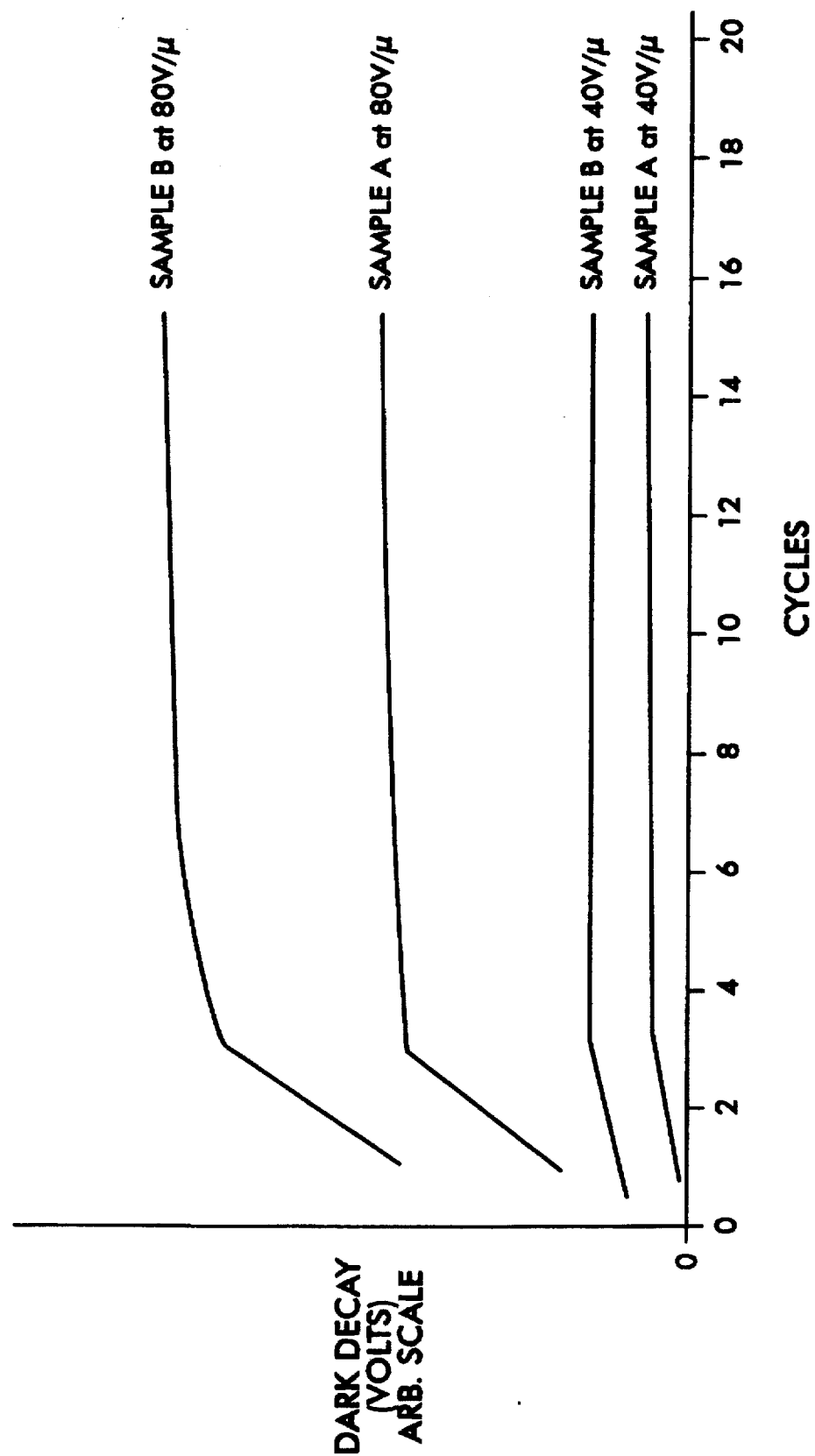
FIG. 4 is a chart illustrating a relationship between dark decay with cycles at two applied fields for two photoreceptors, one acceptable and the other unacceptable.

In FIG. 4, the dark decay versus cycles of two photoreceptors, A and B, are plotted at two fields. The leveling off of dark decay at a crest value after a few cycles is readily apparent for this photoreceptor.

The number of cycles to be run at any step of applied field depends upon the type and quality of photoreceptor tested. In any event, for best results, the number of cycles run should be to about the point where stable dark decay, i.e. a crest dark decay value is attained. Generally, the number of cycles often ranges from about 4 to about 40 cycles. The potential of a photoreceptor decreases even in dark. The potential attained at the development station without the photoreceptor being exposed to light is referred to as Vddp. Typical values of Vddp may be between about 600 and about 1000 volts in a given machine. Vddp registers two types of changes with cycling. In the first change, after initial exposure, the dark decay undergoes changes in a few cycles and thereafter becomes stable at a crest value (see FIGS. 3 and 4). The second is a long term effect which manifests itself as a gradual decrease in Vddp (increase in dark decay) over many tens of kilocycles. It is the initial stable value (crest value) of dark decay which, at the appropriate electrical field, is important in predicting the microdefect level of a photoreceptor in a machine, notwithstanding the fact that the cause for the failure could be for diverse reasons such as poor charge generating layer coating compositions, charge blocking layer coating compositions, charge transport layer coating compositions, process of fabrication and the like.

Figure 5:
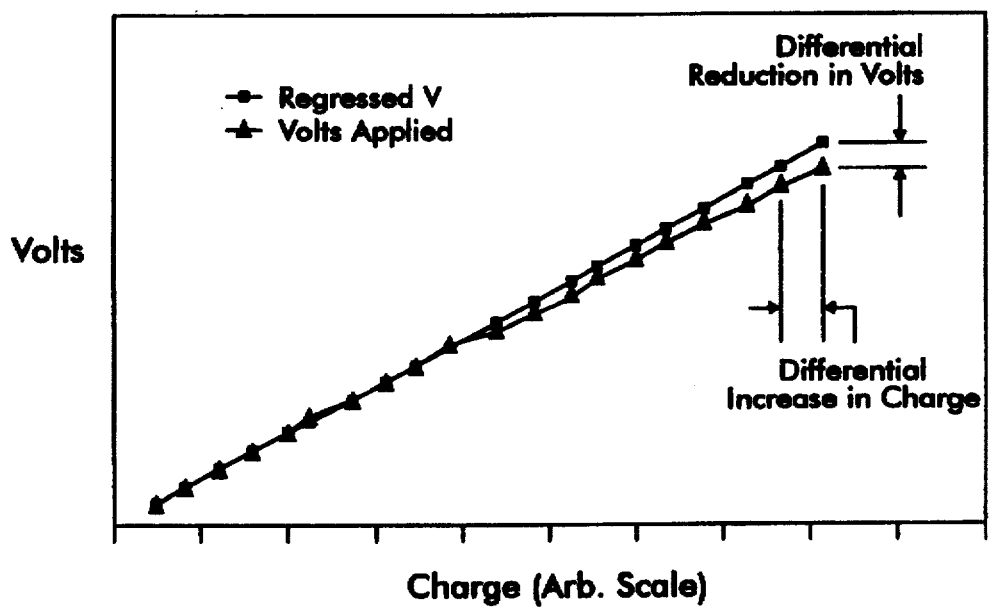
FIG. 5 is a chart illustrating a V-Q relationship for a standard sample and a calculated capacitive V-Q for the same sample. Also shown are definition of DIC and DVR
Figure 6:
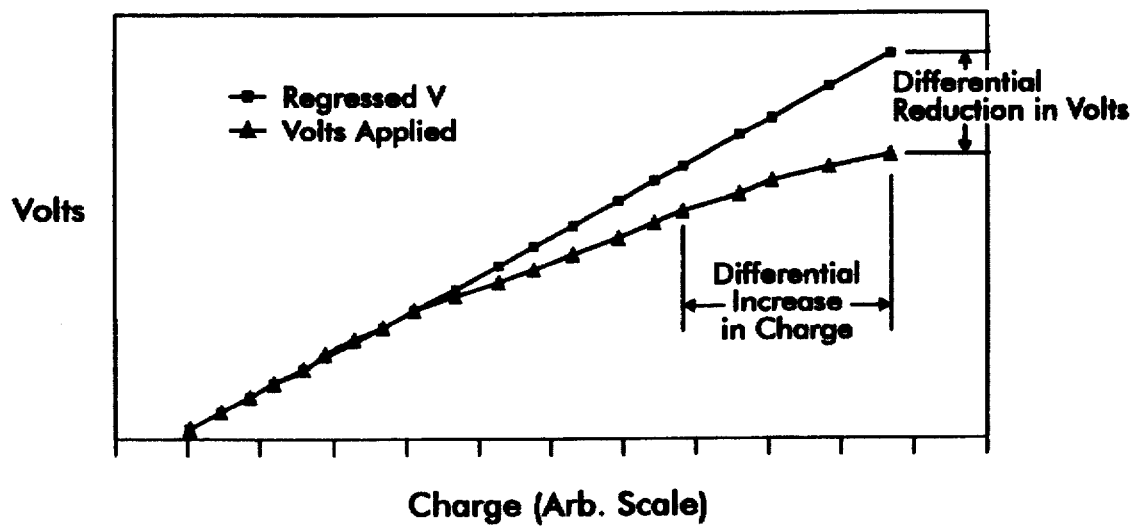
FIG. 6 is a chart showing same for a virgin sample which had an unacceptable level of microdefects. Also shown are definition of DIC and DVR.

Generally, test data is obtained from one or more unused samples from a good batch from which photoreceptors have been successfully tested in actual machine use. This test data is utilized as a control or standard. The differential increase in charge or differential reduction in volts as shown in FIGS. 5 and 6 is found to be a measure of photoreceptor microdefect level in different machines. Generally, this test data involves the identification of an acceptable level of differential increase in charge or differential reduction of voltage as a cut off level standard for a specific machine type and a specific photoreceptor. By performing assessment tests on both long life acceptable photoreceptors and unacceptable photoreceptors for a given type of electrophotographic copier, duplicator or printer, one can establish a reference datum for comparison against newly fabricated photoreceptors to rapidly determine whether the new photoreceptor will have an acceptable or unacceptable machine print quality.

In another embodiment of this invention, the photoreceptor could be charged to high electric fields is by the use of charging devices such as corotron or a scorotron. This could best be accomplished in a fast drum scanner or a flat plate scanner where the photoreceptor sample is passed under the device in a time interval of the order of 10's of milliseconds.

In still another embodiment of this invention a sequence of charging devices such as corotron/scorotron and erase lamps can be installed on manufacturing line. After undergoing a sequence of charge erases as described above, the dark decay can be measured by two electrometers installed spaced apart downstream of the web. The high voltage dark decay obtained can be used for online projection of the life.

For accurate comparisons against a standard, the light exposure and the erase intensities must remain constant. This can be achieved by monitoring the light intensity with a photodiode mounted in the test device housing. The stray light from the sample during the exposure and erase pulses can be measured for light intensity provided the geometrical arrangement is not changed during cycling. This can be achieved by fastening the photodiode to the lid at a suitable location (not shown in the figures). If the light intensity of the light source, for example, a strobotac (available from Gen Rad Inc, Mass. USA) is found to have changed it can be tuned back to the original intensity by inserting appropriate neutral density filters between the light source and the photoreceptor sample. The actinic exposure intensity to be employed depends on the thickness of the transparent metal electrode. Thus, the thickness of the transparent metal electrode is monitored while the metal, e.g. gold, is evaporated onto the photoreceptor surface to form the contact electrode. Further, the light intensity can be indirectly monitored through the electrical characteristics of photoreceptor samples such as the background potential of two or more control samples that were previously tested and archived. The light intensity to be used for both exposure and erase depends on the speed and frequency sensitivities of the photoreceptor sample being tested. Typical light intensities are between about 3 ergs/cm$^2$ and about 20 ergs/cm$^2$ for the exposure step and between about 100 ergs/cm$^2$ and about 1500 ergs/cm$^2$ for the erase step. A typical light frequency range is between about 400 nm to 10000 nm for the spectral sensitivity range of the photoreceptors to be tested. The test system of this invention can also be utilized to predict how a photoreceptor will behave if various conditions during manufacturing are deliberately changed. Thus, for example, it can be utilized to predict the kind of performance a photoreceptor is likely to provide if the formulations of any of the photoreceptor layers is changed or the thickness of any of the layers are varied or if some of the fabrication conditions such as humidity, coating technique and the like are deliberately altered. Generally, armed with the fact that the tested sample exhibits unsatisfactory photoreceptor performance, one may thereafter review manufacturing records to determine whether any unusual events occurred which might affect the ultimate performance of the photoreceptor. For example, a difference in the manner in which one of the photoconductor layer coating composition was prepared or applied may be responsible for the unsatisfactory photoreceptor performance and this problem can promptly be rectified.

Electrostatographic flexible belt imaging members (photoreceptors) are well known in the art. The electrostatographic flexible belt imaging member may be prepared by various suitable techniques. Typically, a transparent flexible substrate is provided having a thin, transparent, electrically conductive surface. At least one photoconductive layer is then applied to the electrically conductive surface. An optional thin charge blocking layer may be applied to the electrically conductive layer prior to the application of the photoconductive layer. If desired, an optional adhesive layer may be utilized between the charge blocking layer and the photoconductive layer. For multilayered photoreceptors, a charge generation layer is usually applied onto the blocking layer and charge transport layer is formed on the charge generation layer.

The substrate is substantially transparent and may comprise numerous suitable materials having the required mechanical properties. Accordingly, the substrate may comprise a layer of an electrically non-conductive or conductive material such as an inorganic or an organic composition. As electrically non-conducting materials there may be employed various resins known for this purpose including polyesters, polycarbonates, polyamides, polyurethanes, and the like which are flexible as thin webs. The electrically insulating or conductive substrate should be flexible and in the form of a flexible web. Preferably, the flexible web substrate comprises a commercially available biaxially oriented polyester known as Mylar, available from E. I. du Pont de Nemours & Co. or Melinex available from ICI.

The thickness of the substrate layer depends on numerous factors, including beam strength and economical considerations, and thus this layer for a flexible belt may be of substantial thickness, for example, about 125 micrometers, or of minimum thickness less than 50 micrometers, provided there are no adverse effects on the final electrostatographic device. In one flexible belt embodiment, the thickness of this layer ranges from about 65 micrometers to about 150 micrometers, and preferably from about 75 micrometers to about 100 micrometers for optimum flexibility and minimum stretch. The surface of the substrate layer is preferably cleaned prior to coating to promote greater adhesion of the deposited coating. Cleaning may be effected, for example, by exposing the surface of the substrate layer to plasma discharge, ion bombardment and the like.

The conductive layer may vary in thickness over substantially wide ranges depending on the optical transparency and degree of flexibility desired for the electrostatographic member. Accordingly, the thickness of the conductive layer may be between about 20 angstroms and about 750 angstrom, and more preferably from about 100 Angstrom units to about 200 angstrom units for an optimum combination of electrical conductivity, flexibility and light transmission. The flexible conductive layer may be an electrically conductive metal layer formed, for example, on the substrate by any suitable coating technique, such as a vacuum depositing technique. Typical metals include aluminum, zirconium, niobium, tantalum, vanadium and hafnium, titanium, nickel, stainless steel, chromium, tungsten, molybdenum, and the like. Typical vacuum depositing techniques include sputtering, magnetron sputtering, RF sputtering, and the like.

If desired, an alloy of suitable metals may be deposited. Typical metal alloys may contain two or more metals such as zirconlure, niobium, tantalum, vanadium and hafnium, titanium, nickel, stainless steel, chromium, tungsten, molybdenum, and the like, and mixtures thereof. Regardless of the technique employed to form the metal layer, a thin layer of metal oxide forms on the outer surface of most metals upon exposure to air. Thus, when other layers overlying the metal layer are characterized as "contiguous" layers, it is intended that these overlying contiguous layers may, in fact, contact a thin metal oxide layer that has formed on the outer surface of the oxidizable metal layer. Generally, for rear erase exposure, a conductive layer light transparency of at least about 15 percent is desirable. The conductive layer need not be limited to metals. Other examples of conductive layers may be combinations of materials such as conductive Indium tin oxide or carbon black loaded polymer with low carbon black concentration as a transparent layer for light having a wavelength between about 4000 Angstroms and about 7000 Angstroms. A typical electrical conductivity for conductive layers for electrophotographic imaging members in slow speed copiers is about $10^2$ to $10^3$ ohms/square.

After formation of an electrically conductive surface, a hole blocking layer may be applied thereto. Generally, electron blocking layers for positively charged photoreceptors allow holes from the imaging surface of the photoreceptor to migrate toward the conductive layer. Any suitable blocking layer capable of forming an electronic barrier to holes between the adjacent photoconductive layer and the underlying conductive layer may be utilized. The blocking layer may be nitrogen containing siloxanes or nitrogen containing titanium compounds such as trimethoxysilyl propylene diamine, hydrolyzed trimethoxysilyl propyl ethylene diamine, N-beta-(aminoethyl) gamma-amino-propyl trimethoxy silane, isopropyl 4-aminobenzene sulfonyl, di(dodecylbenzene sulfonyl) titanate, isopropyl di(4-aminobenzoyl)isostearoyl titanate, isopropyl tri(N-ethylaminoethylamino)titanate, isopropyl trianthranil titanate, isopropyl tri(N,N-dimethyl-ethylamino)titanate, titanium-4-amino benzene sulfonat oxyacetate, titanium 4-aminobenzoate isostearate oxyacetate, [H2N(CH2)4]CH3Si(OCH3)2, (gamma-aminobutyl) methyl diethoxysilane, and [H2N(CH2)3]CH3Si(OCH3)2 (gamma-aminopropyl) methyl diethoxysilane, as disclosed in U.S. Pat. Nos. 4,338,387, 4,286,033 and 4,291,110. The disclosures of U.S. Pat. Nos. 4,338,387, 4,283,033 and 4,291,110 are incorporated herein in their entirety. A preferred blocking layer comprises a reaction product between a hydrolyzed silane and the oxidized surface of a metal ground plane layer. The oxidized surface inherently forms on the outer surface of most metal ground plane layers when exposed to air after deposition. The blocking layer may be applied by any suitable conventional technique such as spraying, dip coating, draw bar coating, gravure coating, silk screening, air knife coating, reverse roll coating, vacuum deposition, chemical treatment and the like. For convenience in obtaining thin layers, the blocking layers are preferably applied in the form of a dilute solution, with the solvent being removed after deposition of the coating by conventional techniques such as by vacuum, heating and the like. The blocking layer should be continuous and have a thickness of less than about 0.2 micrometer because greater thicknesses may lead to undesirably high residual voltage.

An optional adhesive layer may applied to the hole blocking layer. Any suitable adhesive layer well known in the art may be utilized. Typical adhesive layer materials include, for example, polyesters, dupont 49,000 (available from E. I. dupont de Nemours and Company), Vitel PE-100 (available from Goodyear Tire & Rubber), polyurethanes, and the like. Satisfactory results may be achieved with adhesive layer thickness between about 0.05 micrometer (500 angstroms) and about 0.3 micrometer (3,000angstroms). Conventional techniques for applying an adhesive layer coating mixture to the charge blocking layer including spraying, dip coating, roll coating, wire wound rod coating, gravure coating, Bird applicator coating, and the like. Drying of the deposited coating may be effected by any suitable conventional technique such as oven drying, infra red radiation drying, air drying and the like.

Any suitable photogenerating layer may be applied to the adhesive blocking layer which can then be overcoated with a contiguous hole transport layer as described hereinafter. Examples of typical photogenerating layers include inorganic photoconductive particles such as amorphous selenium, trigonal selenium, and selenium alloys selected from the group consisting of selenium-tellurium, selenium-tellurium-arsenic, selenium arsenide and mixtures thereof, and organic photoconductive particles including various phthalocyanine pigment such as the X-form of metal free phthalocyanine described in U.S. Pat. No. 3,357,989, metal phthalocyanines such as vanadyl phthalocyanine and copper phthalocyanine, dibromoanthanthrone, squarylium, quinacridones available from DuPont under the tradename Monastral Red, Monastral violet and Monastral Red Y, Vat orange 1 and Vat orange 3 trade names for dibromo anthanthrone pigments, benzimidazole perylene, substituted 2,4-diaminotriazines disclosed in U.S. Pat. No. 3,442,781, polynuclear aromatic quinones available from Allied Chemical Corporation under the tradename Indofast Double Scarlet, Indofast Violet Lake B, Indofast Brilliant Scarlet and Indofast Orange, and the like dispersed in a film forming polymeric binder. Multi-photogenerating layer compositions may be utilized where a photoconductive layer enhances or reduces the properties of the photogenerating layer. Examples of this type of configuration are described in U.S. Pat. No. 4,415,639, the entire disclosure of this patent being incorporated herein by reference. Other suitable photogenerating materials known in the art may also be utilized, if desired. Charge generating binder layers comprising particles or layers comprising a photoconductive material such as vanadyl phthalocyanine, metal free phthalocyanine, benzimidazole perylene, amorphous selenium, trigonal selenium, selenium alloys such as selenium-tellurium, selenium-tellurium-arsenic, selenium arsenide, and the like and mixtures thereof are especially preferred because of their sensitivity to white light. Vanadyl phthalocyanine, metal free phthalocyanine and tellurium alloys are also preferred because these materials provide the additional benefit of being sensitive to infra-red light.

Any suitable polymeric film forming binder material may be employed as the matrix in the photogenerating binder layer. Typical polymeric film forming materials include those described, for example, in U.S. Pat. No. 3,121,006, the entire disclosure of which is incorporated herein by reference. Thus, typical organic polymeric film forming binders include thermoplastic and thermosetting resins such as polycarbonates, polyesters, polyamides, polyurethanes, polystyrenes, polyarylethers, polyarylsulfones, polybutadienes, polysulfones, polyethersulfones, polyethylenes, polypropylenes, polyimides, polymethylpentenes, polyphenylene sulfides, polyvinyl acetate, polysiloxanes, polyacrylates, polyvinyl acetals, polyamides, polyimides, amino resins, phenylene oxide resins, terephthalic acid resins, phenoxy resins, epoxy resins, phenolic resins, polystyrene and acrylonitrile copolymers, polyvinylchloride, vinylchloride and vinyl acetate copolymers, acrylate copolymers, alkyd resins, cellulosic film formers, poly(amideimide), styrene-butadiene copolymers, vinylidenechloride-vinylchloride copolymers, vinylacetate-vinylidenechloride copolymers, styrene-alkyd resins, polyvinylcarbazole, and the like. These polymers may be block, random or alternating copolymers.

The photogenerating composition or pigment is present in the resinous binder composition in various amounts, generally, however, from about 5 percent by volume to about 90 percent by volume of the photogenerating pigment is dispersed in about 10 percent by volume to about 95 percent by volume of the resinous binder, and preferably from about 20 percent by volume to about 30 percent by volume of the photogenerating pigment is dispersed in about 70 percent by volume to about 80 percent by volume of the resinous binder composition. In one embodiment about 8 percent by volume of the photogenerating pigment is dispersed in about 92 percent by volume of the resinous binder composition.

The photogenerating layer containing photoconductive compositions and/or pigments and the resinous binder material generally ranges in thickness of from about 0.1 micrometer to about 5.0 micrometers, and preferably has a thickness of from about 0.3 micrometer to about 3 micrometers. The photogenerating layer thickness is related to binder content. Higher binder content compositions generally require thicker layers for photogeneration. Thicknesses outside these ranges can be selected providing the objectives of the present invention are achieved.

Any suitable and conventional technique may be utilized to mix and thereafter apply the photogenerating layer coating mixture. Typical application techniques include spraying, dip coating, roll coating, wire wound rod coating, and the like. Drying of the deposited coating may be effected by any suitable conventional technique such as oven drying, infra red radiation drying, air drying and the like.

The active charge transport layer may comprise an activating compound useful as an additive dispersed in electrically inactive polymeric materials making these materials electrically active. These compounds may be added to polymeric materials which are incapable of supporting the injection of photogenerated holes from the generation material and incapable of allowing the transport of these holes therethrough. This will convert the electrically inactive polymeric material to a material capable of supporting the injection of photogenerated holes from the generation material and capable of allowing the transport of these holes through the active layer in order to discharge the surface charge on the active layer. A typical transport layer employed in one of the two electrically operative layers in multilayered photoconductors comprises from about 25 percent to about 75 percent by weight of at least one charge transporting aromatic amine compound, and about 75 percent to about 25 percent by weight of a polymeric film forming resin in which the aromatic amine is soluble. The charge transport layer forming mixture may, for example, comprise an aromatic amine compound of one or more compounds having the general formula:

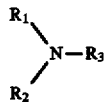

wherein $R_1$ and $R_2$ are an aromatic group selected from the group consisting of a substituted or unsubstituted phenyl group, naphthyl group, and polyphenyl group and $R_3$ is selected from the group consisting of a substituted or unsubstituted aryl group, alkyl group having from 1 to 18 carbon atoms and cycloaliphatic compounds having from 3 to 18 carbon atoms. The substituents should be free form electron withdrawing groups such as $NO_2$ groups, CN groups, and the like. Examples of charge transporting aromatic amines represented by the structural formulae above for charge transport layers capable of supporting the injection of photogenerated holes of a charge generating layer and transporting the holes through the charge transport layer include triphenylmethane, bis(4-diethylamine-2-methylphenyl)phenylmethane; 4'-4"-bis(diethylamino)-2', 2"-dimethyltriphenylmethane, N,N'-bis(alkylphenyl)-[1,1'-biphenyl]-4,4'-diamine wherein the alkyl is, for example, methyl, ethyl, propyl, n-butyl, etc., N,N'-diphenyl-N,N'-bis(chlorophenyl)-[1,1'-biphenyl]-4,4'-diamine, N,N'-diphenyl-N,N'-bis(3"-methylphenyl)-(1,1'-biphenyl)-4,4'-diamine, and the like dispersed in an inactive resin binder.

Any suitable inactive resin binder soluble in methylene chloride or other suitable solvent may be employed in the photoreceptor. Typical inactive resin binders soluble in methylene chloride include polycarbonate resin, polyvinylcarbazole, polyester, polyarylate, polyacrylate, polyether, polysulfone, and the like. Molecular weights can vary, for example, from about 20,000 to about 150,000.

Any suitable and conventional technique may be utilized to mix and thereafter apply the charge transport layer coating mixture to the charge generating layer. Typical application techniques include spraying, dip coating, roll coating, wire wound rod coating, extrusion die coating and the like. Drying of the deposited coating may be effected by any suitable conventional technique such as oven drying, infra red radiation drying, air drying and the like.

Generally, the thickness of the hole transport layer is between about 10 to about 50 micrometers, but thicknesses outside this range can also be used. The hole transport layer should be an insulator to the extent that the electrostatic charge placed on the hole transport layer is not conducted in the absence of illumination at a rate sufficient to prevent formation and retention of an electrostatic latent image thereon. In general, the ratio of the thickness of the hole transport layer to the charge generator layer is preferably maintained from about 2:1 to 200:1 and in some instances as great as 400:1.

Examples of photosensitive members having at least two electrically operative layers include the charge generator layer and diamine containing transport layer members disclosed in U.S. Pat. Nos. 4,265,990, 4,233,384, 4,306,008, 4,299,897 and 4,439,507. The disclosures of these patents are incorporated herein in their entirety. The photoreceptors may comprise, for example, a charge generator layer sandwiched between a conductive surface and a charge transport layer as described above or a charge transport layer sandwiched between a conductive surface and a charge generator layer.

Optionally, an overcoat layer may also be utilized to improve resistance to abrasion. In some cases an anti-curl back coating may be applied to the side opposite the photoreceptor to provide flatness and/or abrasion resistance. These overcoating and anti-curl back coating layers are well known in the art and may comprise thermoplastic organic polymers or inorganic polymers that are electrically insulating or slightly semi-conductive. Overcoatings are continuous and generally have a thickness of less than about 10 micrometers. The thickness of anti-curl backing layers should be sufficient to substantially balance the total forces of the layer or layers on the opposite side of the supporting substrate layer. The total forces are substantially balanced when the belt has no noticeable tendency to curl after all the layers are dried. An example of an anti-curl backing layer is described in U.S. Pat. No. 4,654,284 the entire disclosure of this patent being incorporated herein by reference. A thickness between about 70 and about 160 micrometers is a satisfactory range for flexible photoreceptors.

The assessment process of this invention is a rapid test that does not require extensive machine testing, nor extensive scanner testing, nor numerous reports from repairmen in the field. The simple, rapid test of this invention can, for example, be conducted in a brief ten cycle test. More specifically, the testing process of this invention is very rapid and can complete an assessment in as little as about 5 to 10 minutes compared to several days with scanners, 2 and 3 weeks with machine testing and several months with machines in the field. Moreover, the assessment preformed with the process of this invention is more accurate and free of dilution by unrelated effects due to machine interactions occurring in machine testing.

Since the coating composition for some of the photoconductive layers can significantly affect the ultimate electrical properties and photoreceptor life, it is common practice to test, only one belt from those made with a given batch of coating materials. One batch of coating material can produce many thousands of belts. Thus, a test of one belt represents the testing of many thousands of belts. With the process of the instant invention, samples made with a given batch can rapidly and inexpensively be tested to ensure greater quality control before too large of an inventory of unacceptable belts are produced. This also markedly reduces the amount of photoreceptor material that must be scrapped.

A number of examples are set forth hereinbelow and are illustrative of different compositions and conditions that can be utilized in practicing the invention. All proportions are by weight unless otherwise indicated. It will be apparent, however, that the invention can be practiced with many types of compositions and can have many different uses in accordance with the disclosure above and as pointed out hereinafter.

EXAMPLE I

A photoconductive imaging member was prepared by providing a web of titanium and zirconium coated polyester (Melinex, available from ICI Americas Inc.) substrate having a thickness of 3 mils, and applying thereto, with a gravure applicator, a solution containing 50 grams 3-aminopropyltriethoxysilane, 15 grams acetic acid, 684.8 grams of 200 proof denatured alcohol and 200 grams heptane. This layer was then dried for about 5 minutes at 135° C. in the forced air drier of the coater. The resulting blocking layer had a dry thickness of 500 Angstroms.

An adhesive interface layer was then prepared by the applying a wet coating over the blocking layer, using a gravure applicator, containing 3.5 percent by weight based on the total weight of the solution of copolyester adhesive (49,000, available from Morton Chemical Co., previously available from E. I. du Pont de Nemours & Co.) in a 70:30 volume ratio mixture of tetrahydrofuran/cyclohexanone. The adhesive interface layer was then dried for about 5 minutes at 135° C. in the forced air drier of the coater. The resulting adhesive interface layer had a dry thickness of 620 Angstroms.

A 9 inch×12 inch sample was then cut from the web, and the adhesive interface layer was thereafter coated with a photogenerating layer (CGL) containing 40 percent by volume benzimidazole perylene and 60 percent by volume poly(4,4'-diphenyl-1,1'-cyclohexane carbonate). This photogenerating layer was prepared by introducing 0.3 grams of poly(4,4'-diphenyl-1,1'-cyclohexane carbonate) PCZ -200, available from Mitsubishi Gas Chem. and 48 ml of tetrahydrofuran into a 4 oz. amber bottle. To this solution was added 1.6 gram of benzimidazole perylene and 300 grams of ⅛ inch diameter stainless steel shot. This mixture was then placed on a ball mill for 96 hours. 10 grams of the resulting dispersion was added to a solution containing 0.547 grams of poly(4,4'-diphenyl-1,1'-cyclohexane carbonate) PCZ-200 and 6.14 grams of tetrahydrofuran. The resulting slurry was thereafter applied to the adhesive interface with a ½ mil gap Bird applicator to form a layer having a wet thickness of 0.5 mail. The layer was dried at 135° C. for 5 minutes in a forced air oven to form a dry thickness photogenerating layer having a thickness of about 1.2 micrometers.

This photogenerator layer was overcoated with a charge transport layer. The charge transport layer was prepared by introducing into an amber glass bottle in a weight ratio of a hole transporting molecule of 1:1 N,N'-diphenyl-N,N'-bis (3-methylphenyl)-1,1'-biphenyl-4,4'-diamine and Makrolon 5705, a polycarbonate resin having a molecular weight of from about 50,000 to 100,000 commercially available from Farbenfabriken Bayer A.G. The resulting mixture was dissolved in methylene chloride to form a solution containing 15 percent by weight solids. This solution was applied on the photogenerator layer using a 3-mil gap Bird applicator to form a coating which upon drying had a thickness of 24 microns. During this coating process the humidity was equal to or less than 15 percent. The photoreceptor device containing all of the above layers was annealed at 135° C. in a forced air oven for 5 minutes and thereafter cooled to ambient room temperature.

After application of the charge transport layer coating, the imaging member spontaneous curled upwardly. An anti-curl coating was needed to impart the desired flatness to the imaging member. The anti-curl coating solution was prepared in a glass bottle by dissolving 8.82 grams polycarbonate (Makrolon 5705, available from Bayer AG) and 0.09 grams copolyester adhesion promoter (Vitel PE-100, available from Goodyear Tire and Rubber Company) in 90.07 grams methylene chloride. The glass bottle was then covered tightly and placed on a roll mill for about 24 hours until total dissolution of the polycarbonate and the copolyester is achieved. The anti-curl coating solution thus obtained was applied to the rear surface of the supporting substrate (the side opposite to the imaging layers) by hand coating using a 3 mil gap Bird applicator. The coated wet film was dried at 135° C. in an air circulation oven for about 5 minutes to produce a dry, 14 micrometer thick anti-curl layer and provide the desired imaging member flatness.

This control photoreceptor was machine tested in an electrophotographic duplicator having a pair of photoreceptor belt rollers each having a diameter of about 25 cm. Arranged around the periphery of the photoreceptor belt were conventional processing stations including a charging station, an image exposure station, a development station, a toner image transfer station and an erase station. The duplicator was operated to produce 90 copies per minute. It was found that this photoreceptor performed well to produce acceptable high quality copies for many hundreds of thousands of copies.

A rectangular 2 inches by 4 inches control test sample was prepared from an unused section of the same roll from which the foregoing control photoreceptor belt was prepared. The sample was treated along one edge with methylene chloride solvent to dissolve and remove parts of the charge transfer layer, charge generating layer and adhesive layer to expose part of the electrically conductive layer. A thick strip of electrically conductive silver paint was applied to the exposed surface of the electrically conductive layer for purpose of forming a terminal contact point for application of an electrical bias to the conductive layer. A circular area about 1 cm in diameter on the imaging surface of the photoreceptor not treated with solvent was coated with a thin, transparent vacuum deposited gold layer through a mask or stencil having a circular opening to form another electrode so that an electrical bias can be applied across the photoconductive layers of the photoreceptor from the gold electrode to the electrically conductive layer. This gold electrode had a thickness of about 200 angstroms. The rectangular test sample was tested in a device similar to that illustrated in FIGS. 1 and 2. With a cylindrical lid assembly in an open and load position, the free end of a pivotable electrical connector arm bearing an electrically conductive finger-was pivoted upwardly away from an underlying flat glass on the upper surface of a base assembly. Next, a pivotable flat ground plate having a 4 cm in diameter round opening through its center was pivoted upwardly away from the flat glass upper surface. The pivotable flat ground plate was automatically disconnected from any source of electrical power and remained connected to ground whenever it was raised to either insert or remove a photoreceptor sample. The rectangular sample of flexible photoreceptor was placed on flat glass upper surface and the pivotable flat ground plate was lowered to flatten photoreceptor sample. The raised strip of thick conductive silver coating along one edge of the sample established electrical contact between the electrically conductive layer of the sample and the electrically conductive surface of the pivotable flat ground plate. The circular vacuum deposited metal electrode of gold was encircled by, but not in physical contact with the edge of the round opening in the pivotable flat ground plate. The lowering of the pivotable flat ground plate closed a safety switch and established an electrical connection between the electrically conductive finger and a electromagnetic relay (Model H-152, available from Kilovac) through a 2 megohm resistor. The cylindrical lid assembly was pivoted and lowered to produce a light tight fit between the lid assembly and the base assembly 36. Next, a voltage pulse from a Trek Model 6096-C power supply was applied by activation of the relay for 100 milliseconds, and the dark decay of the photoreceptor sample was measured with a contactless voltage probe (Model 17211, available from Trek) and electrometer (Model 366, available from Trek) during the dark cycle following the voltage pulse, but prior to light being emitted by the erase and exposure lights. The voltage pulse was at a fixed level from one cycle to another during the assessment period. The dark decay measurement was taken at a fixed time period of 1.7 second after termination of the voltage pulse and the measurement was recorded on chart recorder (Model TA2000, available from Gould). The photoreceptor sample was then exposed to an exposure light of about 5 Ergs/cm$^2$ projected downwardly through the circular vacuum deposited gold electrode on the photoreceptor sample. The entire sample was thereafter flood exposed by an Strobotac erase light source (Model GR1538-A, available from GenRad) of about 1000 ergs/cm$^2$ transmitted through the flat glass on the upper surface of a base assembly and through the back surface of the photoreceptor bearing the gold electrode. This cycle of charging, exposing and erasing was repeated for 16 cycles with the alternate cycles having no exposure for recording the dark decay, and the dark decay was plotted against the number of cycles and is shown in FIG. 4 as Curve A and represents a reference datum or control for purposes of rapidly identifying freshly fabricated substandard photoreceptors. After the dark decay reached a crest value the charge was measured through the coloumbmeter at the applied field. The procedure was repeated at the next step of voltage. This was continued until the applied field increased from 4 volts/micron to 80 volts/micron. The data was plotted as shown in FIG. 5. The capacitive Q-V curve as obtained by fitting a straight line for lower values of applied field. Usually this field is lower then 30 volts/ micron. Better value is 20–25 volts/micron. The value of differential increase in charge or differential reduction in voltage can be obtained from the two curves in FIG. 5 at a set point of voltage or charge.

EXAMPLE II

The procedures for preparing a photoreceptor as described in Example I were repeated to form another test sample, except that the charge generator layer was made from a different coating batch which was prepared with the same formulation, but from a different batch of raw materials. This freshly prepared sample was tested in the same manner as that described in Example I. This photoreceptor sample performed poorly in a machine test identical to the machine test described in Example I. The point shows undesirable level of microdefects This machine testing was conducted merely to verify that this rapid assessment technique embodiment of this invention was an effective assessment technique. When samples prepared from the same batch of this photoreceptor material was tested with the technique of this invention, as described in Example I, the dark decay plotted against the number of cycles formed the curve illustrated in FIG. 4 as Curve B. A comparison of Curves A and B demonstrates that poorly performing photoreceptors can rapidly be identified by the technique of this invention without machine testing. The Q-V data for this sample has been shown in FIG. 6. The differential increase in charge level over and above the capacitive value is shown in Figure. This was calculated at the same set point of applied volts (or field) as in Example I. This value is far greater than the value obtained in Example I. Similarly the differential reduction of voltage obtained as shown in FIG. 6 at the same set point of voltage as in Example I. This value is far greater than the corresponding value of Example I.

EXAMPLE III

Figure 7:
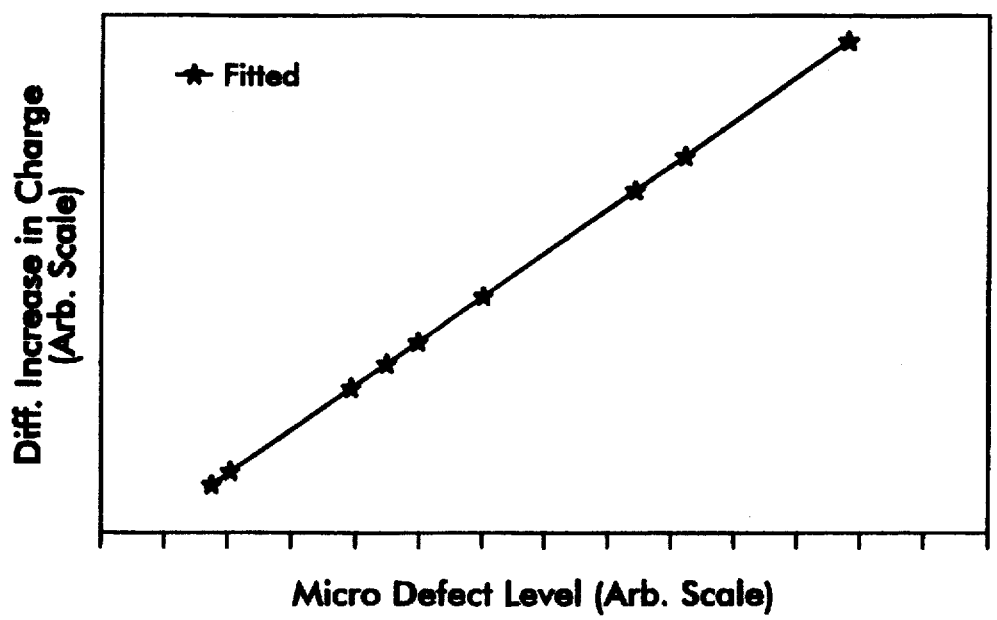
FIG. 7 shows DIC for several batches of photoreceptors vs. the microdefect levels for corresponding photoreceptors.
Figure 8:
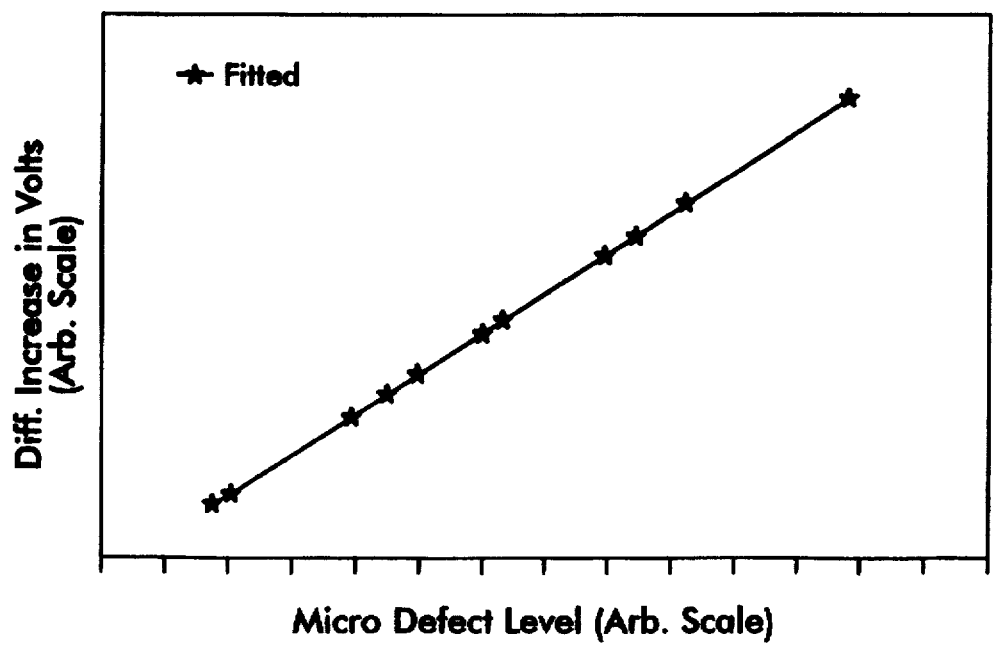
FIG. 8 shows DVR for several batches of photoreceptors vs. the microdefect levels for corresponding photoreceptors.
Figure 9:
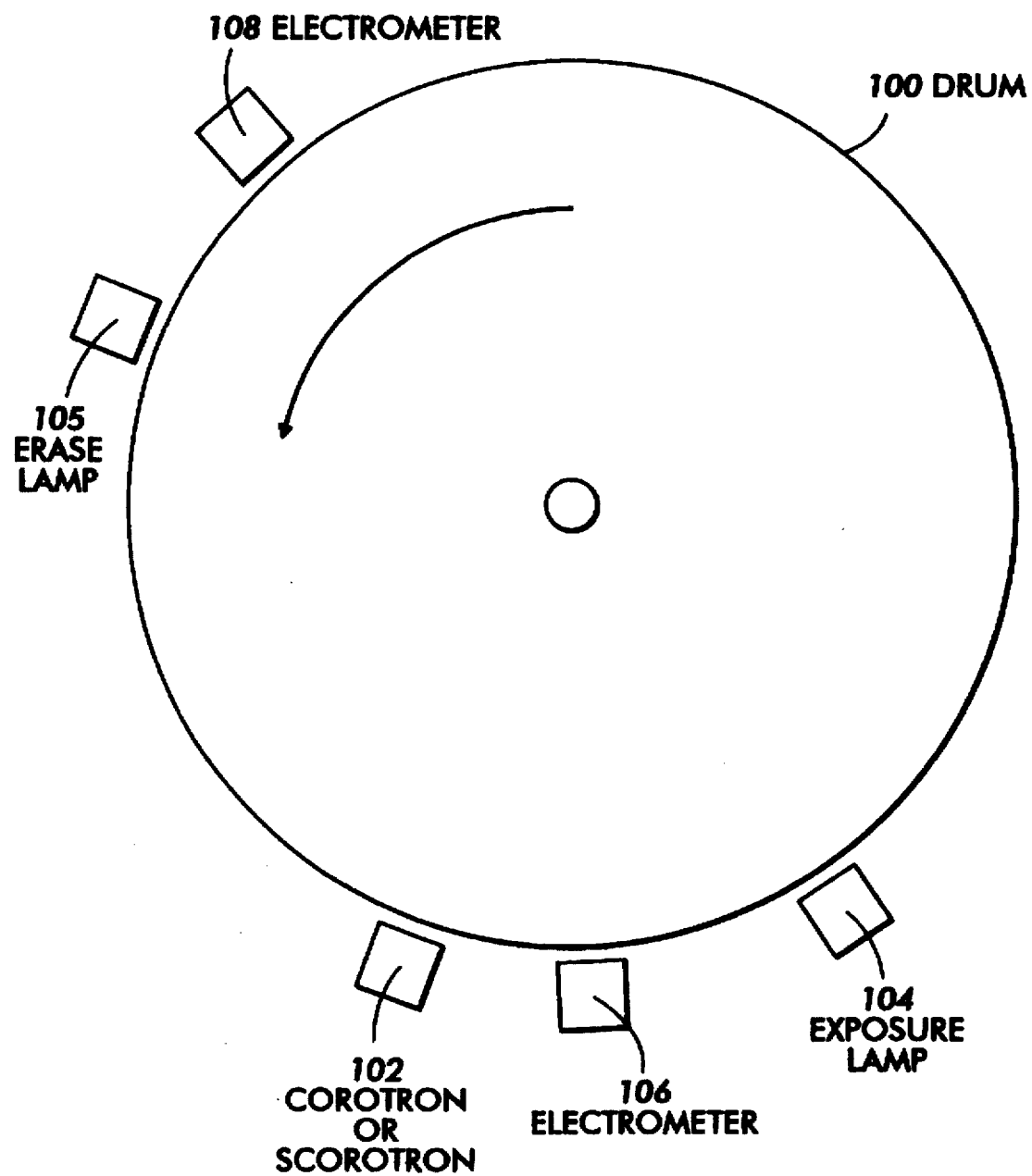
FIG. 9 is a schematic illustration of another embodiment of an apparatus employed in the system of this invention.

Several batches of photoreceptors were analyzed using the technique of this invention as described in Examples I and II over a period of time. The belts fabricated from these batches were tested in printer machines. These gave a widely different levels of micro defect levels. The smaller samples as described in example I and II were tested in the apparatus described in FIG. 2 of the invention and as described in Example I. The values of differential increase in charge above the capacitive level, and differential reductions in voltage below capacitive levels were obtained. The set point for calculating the values were kept same for all the photoreceptors. The differential increase in charge current were plotted against the corresponding micro defect level in FIG. 7. Very good correlation was obtained as seen by regression fit of a straight line. The differential reduction of voltage was plotted against corresponding micro defect level in FIG. 8. Again a very good correlation was obtained as seen by regression fit of a straight line.

Although the invention has been described with reference to specific preferred embodiments, it is not intended to be limited thereto, rather those skilled in the art will recognize that variations and modifications may be made therein which are within the spirit of the invention and within the scope of the claims.

What is claimed is:

1. A process for ascertaining the microdefect levels of an electrophotographic imaging member by comparing the differential reduction in voltage value of a virgin imaging member with that of a known imaging member, the known imaging member having an acceptable level of printed defects, the differential reduction in voltage value being the difference of measured voltage from the voltage needed to capacitively charge the imaging members at a predetermined voltage level.

2. A process for ascertaining the microdefect levels of a virgin electrophotographic imaging member comprising the steps of
   (a) providing at least one reference electrophotographic imaging member comprising an electrically conductive layer and at least one photoconductive layer, the reference imaging member having a known differential increase in charge value, the differential increase in charge value being the excess of charge necessary over and above the charge needed to capacitively charge the imaging members at a predetermined voltage level,
   (b) repeatedly subjecting the reference electrophotographic imaging member to cycles comprising electrostatic charging and light discharging steps while maintaining applied voltage fixed across the reference imaging member, (c) measuring dark decay of the reference imaging member during cycling until the amount of dark decay reaches a stable value, (d) measuring the amount of charge needed to charge the reference imaging member to the fixed voltage when the dark decay has reached a stable value, (e) repeating step (b) with successively increasing applied voltage, (f) repeating step (c) at each selected step of applied voltage, (g) repeating step (d) after step (c) for each selected value of applied voltage in step (e), (h) plotting a graph of volts vs. charge for the reference imaging member, (i) determining the capacitive charging V-Q relationship from the data for the lower voltages of the graph, (j) determining incremental charge needed over and above the charge needed to capacitively charge the imaging member at a predetermined voltage level, the predetermined voltage level being sufficient to give a field where dark decay causes deviation from an extrapolated straight line in a Volt/charge plot for the imaging member, (k) repeatedly subjecting a virgin electrophotographic imaging member to the aforementioned steps from (a) through (j), (l) establishing for the virgin electrophotographic imaging member a datum for differential increase in charge over and above the charge needed to capacitively charge the imaging member at a predetermined voltage level, the voltage levels at which the calculation is made being the same as in step (j) for the standard imaging member, and (m) comparing the differential increase in charge of the virgin electrophotographic imaging member with the known differential increase in charge value to ascertain the projected microdefect levels of the virgin imaging member.

3. A process for ascertaining the microdefect levels of a virgin electrophotographic imaging member comprising the steps of providing a reference imaging member and a virgin imaging member, measuring departure from an extrapolated straight line in a Volt/charge plot for the reference imaging member, measuring departure from the extrapolated straight line in the Volt/charge plot for the virgin imaging member and comparing (a) increase in departure of charge in the plot for the virgin member over and above the departure of charge in the plot for the reference imaging member for a predetermined voltage value or (b) reduction in departure of voltage in the plot for the reference imaging member below the departure of voltage in the plot for the virgin imaging member for a predetermined charge value.

4. A process for ascertaining the microdefect levels of a virgin electrophotographic imaging member by comparing the differential increase in charge value of the virgin imaging member with the differential increase in charge value of a reference imaging member, the reference imaging member having an acceptable level of printed defects, the differential increase in charge value being the excess of charge necessary over and above the charge needed to capacitively charge the imaging members at a predetermined voltage level.

5. A process for ascertaining the microdefect levels of a virgin electrophotographic imaging member comprising the steps of (a) providing at least one reference electrophotographic imaging member comprising an electrically conductive layer and at least one photoconductive layer, the reference imaging member having a known differential increase in voltage value, the differential increase in voltage value being the excess of voltage necessary over and above the voltage needed to capacitively charge the imaging members at a predetermined charge level, (b) repeatedly subjecting the first electrophotographic imaging member to cycles comprising electrostatic charging and light discharging steps while maintaining the applied voltage fixed across the reference imaging member, (c) measuring dark decay of the reference imaging member during cycling until the amount of dark decay reaches a stable value, (d) measuring the amount of charge needed to charge the reference imaging member to the fixed voltage when the dark decay has reached a stable value, (e) repeating step (b) with successively increasing applied voltage, (f) repeating step (c) at each selected step of applied voltage, (g) repeating step (d) after step (c) for each selected value of applied voltage in step (e), (h) plotting a graph of volts vs. charge for the first imaging member, (i) determining the capacitive charging V-Q relationship from the data for the lower voltages of the graph, (j) establishing for the reference imaging member a datum for differential reduction in voltage below the voltage needed to capacitively charge the imaging members at a predetermined charge level, the predetermined charge level being sufficient to give a field where dark decay causes deviation from an extrapolated straight line in a Volt/charge plot for the reference imaging member, (k) repeatedly subjecting a virgin imaging member to the aforementioned steps from (a) through (i), and (l) establishing for the virgin imaging member a datum for differential reduction in voltage below the voltage needed to capacitively charge the imaging members at a predetermined voltage level to a higher predetermined charge level, the value of charge at which the calculation is made being the same as in step (j) for the reference imaging member.

6. A process for ascertaining the microdefect levels of a virgin electrophotographic imaging member according to claim 1 wherein said dark decay reaches a stable value when the change in dark decay during cycling is less than about 10 volts from cycle to cycle.

7. A process for ascertaining the microdefect levels of a virgin electrophotographic imaging member according to claim 2 wherein said dark decay reaches a stable value when the change in dark decay during cycling is less than about 10 volts from cycle to cycle.

8. A process for ascertaining the microdefect levels of a virgin electrophotographic imaging member according to claim 2 wherein the high field in step (j) is between about 60 v/micrometer to about 80 volts/micrometer.

9. A process for ascertaining the microdefect levels of a virgin electrophotographic imaging member according to claim 8 wherein the datum for differential reduction in voltage below the charge needed to capacitively charge the imaging member at a predetermined charge is calculated at a charge which gives rise to a field between about 60 volts/micrometer to 80 volts/micrometer.

* * * * *